(12) United States Patent
Pettersson

(10) Patent No.: US 8,470,361 B2
(45) Date of Patent: Jun. 25, 2013

(54) NON-ABUSABLE PHARMACEUTICAL COMPOSITION COMPRISING OPIOIDS

(75) Inventor: Anders Pettersson, Uppsala (SE)

(73) Assignee: Orexo AB, Uppsala (SE)

( * ) Notice: Subject to any disclaimer, the term of this patent is extended or adjusted under 35 U.S.C. 154(b) by 681 days.

(21) Appl. No.: 12/312,995

(22) PCT Filed: Dec. 3, 2007

(86) PCT No.: PCT/GB2007/004627
§ 371 (c)(1),
(2), (4) Date: Jan. 12, 2010

(87) PCT Pub. No.: WO2008/068471
PCT Pub. Date: Jun. 12, 2008

(65) Prior Publication Data
US 2010/0129443 A1   May 27, 2010

Related U.S. Application Data

(60) Provisional application No. 60/872,496, filed on Dec. 4, 2006.

(51) Int. Cl.
*A61F 13/00* (2006.01)

(52) U.S. Cl.
USPC ........... 424/435; 424/464; 424/465; 424/489; 424/490; 514/282; 514/329

(58) Field of Classification Search
None
See application file for complete search history.

(56) References Cited

U.S. PATENT DOCUMENTS

| | | | | |
|---|---|---|---|---|
| 6,759,059 | B1 * | 7/2004 | Pettersson et al. | ............ 424/489 |
| 2003/0124061 | A1 | 7/2003 | Roberts | |
| 2003/0124185 | A1 * | 7/2003 | Oshlack et al. | ............... 424/465 |
| 2003/0191147 | A1 | 10/2003 | Sherman et al. | |
| 2004/0180916 | A1 | 9/2004 | Levine | |

FOREIGN PATENT DOCUMENTS

| | | |
|---|---|---|
| EP | 0144243 | 4/1989 |
| EP | 1299104 | 4/2003 |
| WO | WO0016750 | 3/2000 |
| WO | WO0016751 | 3/2000 |
| WO | WO02092060 | 11/2002 |
| WO | WO2004067004 | 8/2004 |
| WO | WO2004093801 | 11/2004 |
| WO | WO2006103418 | 10/2006 |

OTHER PUBLICATIONS

P.J. Fudala, et al. Drug and Alcohol Dependence; 83S, S40-S47, 2006.
Staniforth, Powder Technol., 45, 73, 1985.
G. Sala, Proceed. Int. Symb. Contr. Release Bioact, Mat, 16, 420, 1989.
Lachman et al., The Theory and Practice of Industrial Pharmacy, Lea & Febiger, 3$^{rd}$ Edition, 1986.
Remington: The Science and Practice of Pharmacy, Gennaro (Ed.), Philadelphia College of Pharmacy and Sciences, 19$^{th}$ Edition (1995).
Pharmaceutical Dosage Forms: Tablets, vol. 1, 2$^{nd}$ Edition, Lieberman et al., (Eds.), Marcel Dekker, New York and Basel (1989) p. 354-356.
S. McColl, et al., Drug and Alcohol Dependence, 83S, 2006, S52-S62.

\* cited by examiner

*Primary Examiner* — Hasan Ahmed
(74) *Attorney, Agent, or Firm* — Covington & Burling LLP

(57) ABSTRACT

There is provided pharmaceutical compositions for the treatment of pain comprising a pharmacologically-effective amount of an opioid analgesic, or a pharmaceutically-acceptable salt thereof, presented in particulate form upon the surfaces of carrier particles comprising a pharmacologically-effective amount of an opioid antagonist, or a pharmaceutically-acceptable salt thereof, which carrier particles are larger in size than the particles of the opioid analgesic. The compositions are also useful in prevention of opioid abuse by addicts.

19 Claims, No Drawings

NON-ABUSABLE PHARMACEUTICAL COMPOSITION COMPRISING OPIOIDS

This application is the National Stage of international patent application Serial No. PCT/GB2007/004627, filed on Dec. 3, 2007, which claims priority under 35 U.S.C. §119(e) to U.S. provisional patent application Ser. No. 60/872,496, filed on Dec. 4, 2006.

This invention relates to new, fast acting, non-abusable pharmaceutical compositions that are useful in the treatment of pain, which compositions may be administered transmucosally and in particular sublingually.

Opioids are widely used in medicine as analgesics. Indeed, it is presently accepted that, in the palliation of more severe pain, no more effective therapeutic agents exist.

The term "opioid" is typically used to describe a drug that activates opioid receptors, which are found in the brain, the spinal cord and the gut. Three classes of opioids exist:

(a) naturally-occurring opium alkaloids. These include morphine and codeine;
(b) compounds that are similar in their chemical structure to the naturally-occurring opium alkaloids. These so-called semi-synthetics are produced by chemical modification of the latter and include the likes of diamorphine (heroin), oxycodone and hydrocodone; and
(c) truly synthetic compounds such as fentanyl and methadone. Such compounds may be completely different in terms of their chemical structures to the naturally-occurring compounds.

Of the three major classes of opioid receptors ($\mu$, $\kappa$ and $\delta$), opioids' analgesic and sedative properties mainly derives from agonism at the $\mu$ receptor.

Opioid analgesics are used to treat the severe, chronic pain of terminal cancer, often in combination with non-steroid anti-inflammatory drugs (NSAIDs), as well as acute pain (e.g. during recovery from surgery). Further, their use is increasing in the management of chronic, non-malignant pain.

Opioid-requiring cancer patients are usually given slow-release opiates (slow-release morphine or ketobemidone, or transdermal fentanyl). A characteristic feature of such treatments is periods of inadequate analgesia (so-called "breakthrough" pain). Such periods are thought to be due to increased physical activity of the patient. However, treatment of breakthrough pain by administration of increased time-contingent doses of long-acting analgesic formulations is known to cause, adverse side effects, including excess sedation, nausea, and constipation.

Presently-available oral, rectal and sublingual opioid analgesic formulations have relatively lengthy onset times and/or erratic absorption characteristics, which makes then not entirely suitable for the control of acute and/or breakthrough pain.

In order to obtain rapid onset of analgesia in the treatment of other types of acute pain, including operative pain, post-operative pain, traumatic pain, post-traumatic pain, and pain caused by severe diseases, such as myocardial infarction, nephrolithiasis, etc., opioid analgesics are often administered parenterally (e.g. by intravenous or intramuscular injection). However, injections are an unpopular mode of administration, often being regarded as inconvenient and painful.

In view of the above, there is a real and growing clinical need for fast-acting orally-delivered drug compositions comprising opioid analgesics. In particular, a need exists for further or better fast-acting formulations comprising opioid analgesics, which may be administered by a convenient route, for example transmucosally, particularly, as is usually the case, when such active ingredients are incapable of being delivered perorally due to poor and/or variable bioavailability.

However, a perennial problem with potent opioid analgesics such as fentanyl is one of abuse by drug addicts. Addicts normally abuse pharmaceutical formulations by extracting a large quantity of active ingredient from that formulation into solution, which is then injected intravenously. With most commercially-available pharmaceutical formulations, this can be done relatively easily, which renders them unsafe or "abusable". Thus, there also is a need for a fast acting, non-abusable pharmaceutical formulation comprising opioid analgesics.

Naloxone is a selective opioid antagonist that is used to reverse the pharmacological effects of opioids. Naloxone may therefore be used to treat narcotic drug overdose or to diagnose suspected opioid addiction. Naloxone has poor bioavailability when administered transmucosally but has good bioavailability when administered by injection.

A simple mixture combination of the opioid partial agonist buprenorphine and naloxone for sublingual administration is available under the trademark Suboxone®. This and other abuse-resistant opioid-containing formulations are reviewed by Fudula and Johnson in *Drug and Alcohol Dependence*, 83S, S40 (2006). See also US patent applications US 2003/0124061 and US 2003/0191147.

International patent applications WO 00/16750, WO 2004/067004 and WO 2006/103418, all disclose drug delivery systems for the treatment of e.g. acute pain by sublingual administration in which the active ingredient in microparticulate form and is adhered to the surface of larger carrier particles in the presence of a bioadhesive and/or mucoadhesive promoting agent. Specific combinations of opioid analgesics and opioid antagonists are not mentioned or suggested anywhere in these documents.

In endeavouring to solve the above-mentioned problems, and to provide an improved, effective, fast-acting, non-abusable bioadhesive formulation comprising a potent opioid analgesic, such as fentanyl, in combination with a sufficient dose of an opioid antagonist, such as naloxone, we have found that it is not possible to provide both active ingredients upon the surfaces of inert carrier particles as disclosed in the aforementioned patent documents. We have therefore devised an elegant solution to this problem by providing particles of opioid analgesic drug upon the surfaces of carrier particles comprising an opioid antagonist, such as naloxone.

According to a first aspect of the invention there are provided particulate pharmaceutical compositions for the treatment of pain comprising a pharmacologically-effective amount of an opioid analgesic, or a pharmaceutically-acceptable salt thereof, presented in particulate form upon the surfaces of carrier particles comprising a pharmacologically-effective amount of an opioid antagonist, or a pharmaceutically-acceptable salt thereof, which carrier particles are larger in size than the particles of the opioid analgesic, which compositions are referred to hereinafter as "the compositions of the invention".

Compositions of the invention may further comprise a bioadhesion and/or a mucoadhesion promoting agent, which agent is, at least in part, presented on the surfaces of the carrier particles.

The compositions of the invention are interactive mixtures. The term "interactive" mixture will be understood by those skilled in the art to denote a mixture in which particles do not appear as single units, as in random mixtures, but rather where smaller particles (of, for example, opioid analgesic and/or bioadhesion and/or mucoadhesion promoting agent)

are attached to (i.e. adhered to or associated with) the surfaces of larger opioid antagonist-containing, or opioid antagonist-based, carrier particles. Such mixtures are characterised by interactive forces (for example van der Waals forces, electrostatic or Coulombic forces, and/or hydrogen bonding) between carrier and surface-associated particles (see, for example, Staniforth, *Powder Technol.*, 45, 73 (1985)). In the final mixture, the interactive forces need to be strong enough to keep the adherent particles at the carrier surface, in order to create a homogeneous mixture.

The term "opioid analgesic" will be understood by the skilled person to include any substance, whether naturally-occurring or synthetic, with opioid or morphine-like properties and/or which binds to opioid receptors, particularly the µ-opioid receptor, having at least partial agonist activity, thereby capable of producing an analgesic effect.

Opioid analgesics that may be mentioned include opium derivatives and the opiates, including the naturally-occurring phenanthrenes in opium (such as morphine, codeine, thebaine and Diels-Alder adducts thereof) and semisynthetic derivatives of the opium compounds (such as diamorphine, hydromorphone, oxymorphone, hydrocodone, oxycodone, etorphine, nicomorphine, hydrocodeine, dihydrocodeine, metopon, normorphine and N-(2-phenylethyl)normorphine). Other opioid analgesics that may be mentioned include fully synthetic compounds with opioid or morphine-like properties, including morphinan derivatives (such as racemorphan, levorphanol, dextromethorphan, levallorphan, cyclorphan, butoiphanol and nalbufine); benzomorphan derivatives (such as cyclazocine, pentazocine and phenazocine); phenylpiperidines (such as pethidine (meperidine), fentanyl, alfentanil, sufentanil, remifentanil, ketobemidone, carfentanyl, anileridine, piminodine, ethoheptazine, alphaprodine, betaprodine, 1-methyl-4-phenyl-1,2,3,6-tetrahydropyridine (MPTP), diphenoxylate and loperamide), phenylheptamines or "open chain" compounds (such as methadone, isomethadone, propoxyphene and levomethadyl acetate hydrochloride (LAAM)); diphenylpropylamine derivatives (such as dextromoramide, piritramide, bezitramide and dextropropoxyphene); mixed agonists/antagonists (such as buprenorphine, nalorphine and oxilorphan) and other opioids (such as tilidine, tramadol and dezocine). More preferred opioid analgesics include buprenorphine, alfentanil, sufentanil, remifentanil and, particularly, fentanyl.

The term "opioid antagonist" will be understood by the skilled person to include any substance, whether naturally-occurring or synthetic, which binds to opioid receptors, particularly the µ-opioid receptor, having at least partial antagonist activity, thereby for example at least partially reversing one or more of the pharmacological effects of an opioid analgesic mentioned hereinbefore. Opioid antagonists that may be mentioned include naloxone, cyclazocine, nalmefene, opioid antagonist compounds having the same pentacyclic nucleus as nalmefene, naltrexone, methylnaltrexone, nalorphine, nalbuphine, thebaine, levallorphon, pentazocine, oxymorphine, butorphanol, bupremorphine, levorphanol, meptazinol, dezocine, or pentazocine or their pharmacologically effective salts or esters such as, but not limited to, their hydrochlorides, maleates, tartrates and lactates. Preferred opioid antagonists include nalmefene, preferably methylnaltrexone, more preferably naltrexone and, particularly, naloxone.

Any of the active ingredients mentioned in the above groupings may also be used in combination as required. Moreover, the above active ingredients may be used in free form or, if capable of forming salts, in the form of a salt with a suitable acid or base. If the drugs have a carboxyl group, their esters may be employed. Active ingredients can be used as racemic mixtures or as single enantiomers.

The term "pharmacologically effective amount" refers to an amount of an active ingredients, which is capable of conferring a desired therapeutic effect on a treated patient, whether administered alone or in combination with another active ingredient. Such an effect may be objective (i.e. measurable by some test or marker) or subjective (i.e. the subject gives an indication of, or feels, an effect).

Appropriate pharmacologically effective amounts of opioid analgesic compounds include those that are capable of producing (preferably rapid) relief of pain when administered transmucosally, whereas appropriate pharmacologically effective amounts of opioid antagonist compounds in the carrier particles must be sufficient so as not to compete with the pain-relieving effect of the opioid analgesic present in the composition of the invention upon transmucosal administration, but to block the effect of the opioid analgesic if an attempt is made by an opioid-addicted individual to inject a composition of the invention. As stated above, we have found that this can be achieved elegantly by presenting smaller microparticles of opioid analgesic on the surfaces of larger carrier particles comprising opioid antagonist, and the skilled person will appreciate that the relative sizes of the two active ingredients can be utilised to achieve the necessary relevant doses in this respect.

The amounts of active ingredients that may be employed in compositions of the invention may thus be determined by the physician, or the skilled person, in relation to what will be most suitable for an individual patient. This is likely to vary with the route of administration, the type and severity of the condition that is to be treated, as well as the age, weight, sex, renal function, hepatic function and response of the particular patient to be treated.

The total amount of opioid analgesic active ingredient that may be employed in a composition of the invention will depend upon the nature of the relevant active ingredient that is employed, but may be in the range of about 0.0005%, such as about 0.1% (e.g. about 1%, such as about 2%) to about 20%, such as about 10%, for example about 7%, by weight based upon the total weight of the composition. The amount of this active ingredient may also be expressed as the amount in a unit dosage form (e.g. a tablet). In such a case, the amount of opioid analgesic active ingredient that may be present may be sufficient to provide a dose per unit dosage form that is in the range of between about 1 µg (e.g. about 5 µg) and about 20 mg (e.g. about 15 mg, such as about 10 mg).

The total amount of opioid antagonist that may be employed in a composition of the invention may be in the range about 1%, such as about 2% (e.g. about 5%, such as about 10%) to about 98%, such as about 99%, for example about 99.9% (e.g. 99.9995%). The amount of this active ingredient may also be expressed as the amount in a unit dosage form (e.g. a tablet). In such a case, the amount of opioid antagonist active ingredient that may be present may be sufficient to provide a dose per unit dosage form that is in the range of between about 0.1 mg and about 10 mg, such as about 1 to about 5 mg (e.g. about 4 mg).

The above-mentioned dosages are exemplary of the average case; there can, of course, be individual instances where higher or lower dosage ranges are merited, and such are within the scope of this invention.

Opioid analgesic active ingredients in the compositions of the invention are preferably in the form of microparticles, preferably with a weight based mean diameter of between about 0.5 µm and about 15 µm, such as about 1 µm and about 10 µm. The term "weight based mean diameter" will be understood by the skilled person to include that the average particle size is characterised and defined from a particle size distribution by weight, i.e. a distribution where the existing fraction (relative amount) in each size class is defined as the weight fraction, as obtained e.g. by sieving.

Microparticles of active ingredients may be prepared by standard micronisation techniques, such as grinding, dry milling, wet milling, precipitation, etc.

Preferably, opioid antagonist-containing carrier particles for use in compositions of the invention are of a size that is between about 50 and about 1000 μm (e.g. about 800 μm, such as about 750 μm), and preferably between about 100 and about 600 μm.

It is possible for certain active ingredients that the relative sizes and amounts of the particles of opioid analgesic active ingredient and the opioid antagonist-containing carrier particles that are employed are sufficient to ensure that the carrier particles may be at least about 90% covered by the opioid analgesic, for example at least about 100% and up to about 200% (e.g. between about 130% and about 180%) covered. The skilled person will appreciate in this context that "100% coverage" of the carrier particles by the opioid analgesic means that the relative particle sizes and amounts of the relevant particles that are employed are sufficient to ensure that the entire surface area of each carrier particle could be covered by particles of the opioid analgesic notwithstanding that other ingredients (e.g. mucoadhesion promoting agent) may also be present in a composition. Obviously, if other such ingredients are employed, then the actual degree of coverage of carrier particles by active ingredient may be less than the amounts specified above. 200% coverage means that there is sufficient particles of opioid analgesic to cover the surfaces of the carrier particles twice over, notwithstanding the presence of other ingredients.

It is surprising that compositions with greater than 90% theoretical coverage are effective. Based on current knowledge, the skilled person would understand that, in order to ensure rapid dissolution, it would be important to ensure that the relative sizes/amounts of opioid analgesic/carrier particles are sufficient to ensure that 70% or less of the surfaces of the latter could be covered by the former.

As mentioned hereinbefore, compositions of the invention may comprise one or more bioadhesion and/or mucoadhesion promoting agent at least in part presented on, and/or adhered to, the surface of an opioid antagonist-containing carrier particle, and may thus facilitate the partial or complete adhesion of active ingredients to a biological surface, such as a mucosal membrane.

The terms "mucoadhesive" and "mucoadhesion" refer to adhesion or adherence of a substance to a mucous membrane within the body, wherein mucous is present on the surface of that membrane (e.g. the membrane is substantially (e.g. >95%) covered by mucous). The terms "bioadhesive" and "bioadhesion" refer to adhesion or adherence of a substance to a biological surface in a more general sense. Biological surfaces as such may include mucous membranes wherein mucous is not present on that surface, and/or surfaces that are not substantially (e.g. <95%) covered by mucous. The skilled person will appreciate that, for example, the expressions "mucoadhesion" and "bioadhesion" may often be used interchangeably. In the context of the present invention, the relevant terms are intended to convey a material that is capable of adhering to a biological surface when placed in contact with that surface (in the presence of mucous or otherwise) in order to enable compositions of the invention to adhere to that surface. Such materials are hereinafter referred to together as "bio/mucoadhesives" or "bio/mucoadhesion promoting agents", and such properties together as "bio/mucoadhesion" or "bio/mucoadhesive".

A variety of polymers known in the art can be used as bio/mucoadhesion promoting agents, for example polymeric substances, preferably with an average (weight average) molecular weight above 5,000. It is preferred that such materials are capable of rapid swelling when placed in contact with water and/or, more preferably, mucous, and/or are substantially insoluble in water at room temperature and atmospheric pressure.

Bio/mucoadhesive properties may be routinely determined in a general sense in vitro, for example as described by G. Sala et al in *Proceed. Int. Symp. Contr. Release. Bioact. Mat.*, 16, 420, 1989. Examples of suitable bio/mucoadhesion promoting agents include cellulose derivatives such as hydroxypropylmethyl cellulose (HPMC), hydroxyethyl cellulose (HEC), hydroxypropyl cellulose (HPC), methyl cellulose, ethyl hydroxyethyl cellulose, carboxymethyl cellulose, modified cellulose gum and sodium carboxymethyl cellulose (NaCMC); starch derivatives such as moderately cross-linked starch, modified starch and sodium starch glycolate; acrylic polymers such as carbomer and its derivatives (Polycarbophyl, Carbopol®, etc.); polyvinylpyrrolidone; polyethylene oxide (PEO); chitosan (poly-(D-glucosamine)); natural polymers such as gelatin, sodium alginate, pectin; scleroglucan; xanthan gum; guar gum; poly co-(methylvinyl ether/maleic anhydride); and crosscarmellose (e.g. crosscarmellose sodium). Such polymers may be crosslinked. Combinations of two or more bio/mucoadhesive polymers can also be used.

Suitable commercial sources for representative bio/mucoadhesive polymers include: Carbopol® acrylic copolymer (BF Goodrich Chemical Co, Cleveland, 08, USA); HPMC (Dow Chemical Co., Midland, Mich., USA); NEC (Natrosol; Hercules Inc., Wilmington, Del. USA); HPC (Klucel®; Dow Chemical Co., Midland, Mich., USA); NaCMC (Hercules Inc. Wilmington, Del. USA); PEO (Aldrich Chemicals, USA); sodium alginate (Edward Mandell Co., Inc., Carmel, N.Y., USA); pectin (BF Goodrich Chemical Co., Cleveland, Ohio, USA); crosslinked polyvinylpyrrolidone (Kollidon CL®, BASF, Germany, Polyplasdone XL®, Polyplasdone XL-10® and Polyplasdone INF-10®, ISP Corp., US); Ac-Di-Sol® (modified cellulose gum with a high swellability; FMC Corp., USA); Actigum (Mero-Rousselot-Satia, Baupte, France); Satiaxana (Sanofi BioIndustries, Paris, France); Gantrez® (ISP, Milan, Italy); chitosan (Sigma, St Louis, Miss., USA); and sodium starch glycolate (Primojel®, DMV International BV, Netherlands, Vivastar®, J. Rettenmaier & Söhne GmbH & Co., Germany, Explotab®, Roquette America, US).

Preferred bio/mucoadhesion promoting agents that may be employed in compositions of the invention include internally crosslinked sodium carboxymethylcellulose, such as croscarmellose sodium NF (e.g. Ac-Di-Sol® (FMC Corp., USA)) and crosslinked polyvinylpyrollodine (e.g. Kollidon CL®, BASF, Germany).

Depending on the type of the bio/mucoadhesion promoting agent used, the rate and intensity of bio/mucoadhesion may be varied.

Suitably, the amount of bio/mucoadhesion promoting agent that is present in a composition of the invention may be in the range of about 0.1 to about 25% by weight based upon the total weight of the composition. A preferred range is from about 0.5 to about 15% by weight, such as about 1 to about 10% (e.g. about 2 to about 8%) by weight.

The carrier particles that are employed in compositions of the invention comprise opioid antagonist as defined herein.

Carrier particles may or may not consist essentially of opioid antagonist. By "consisting essentially" of opioid antagonist, we mean that the carrier particles comprise at least about 95%, such as at least about 98%, more preferably greater than about 99%, and particularly at least about 99.5% by weight (based on the total weight of the carrier particle) of such an antagonist. These percentages exclude the presence of trace amounts of water and/or any impurities that may be present in such materials, which impurities may arise following the production of such materials, either by a commercial or non-commercial third party supplier, or by a skilled person making a composition of the invention. In any event, the possibility of particles of opioid antagonist also being presented, at least in part, upon the surfaces of, and/or between, such carrier particles is not excluded.

When the carrier particles do not consist essentially of opioid antagonist, additional materials that may also form part of the carrier particles include pharmaceutically-acceptable substances, such as carbohydrates, e.g. sugar, mannitol and lactose; pharmaceutically-acceptable inorganic salts, such as sodium chloride, calcium phosphate, dicalcium phosphate hydrate, dicalcium phosphate dehydrate, tricalcium phosphate, calcium carbonate, and barium sulfate; polymers, such as microcrystalline cellulose, cellulose and crosslinked polyvinylpyrrolidone; or mixtures thereof.

When carrier particles do not consist essentially of opioid antagonist, additional materials may be admixed together with opioid antagonist by a variety of techniques, such as dry mixing, extrusion and/or spheronisation, or a process of granulation, which may comprise wet and/or dry granulation.

Wet granulation techniques are well known to those skilled in the art and include any technique involving the massing of a mix of dry primary powder particles using a granulating fluid, which fluid comprises a volatile, inert solvent, such as water, ethanol or isopropanol, either alone or in combination, and optionally in the presence of a binder or binding agent. The technique may involve forcing a wet mass through a sieve to produce pellets by spheronisation or wet granules which are then dried. Dry granulation techniques are also well known to those skilled in the art and include any technique in which primary powder particles are aggregated under high pressure, including slugging and roller compaction, for example as described hereinafter.

Primary particles of ingredients (e.g. opioid antagonist and other carrier particle materials) may be processed by techniques, such as grinding, dry milling, wet milling, precipitation, etc, prior to granulation.

Granulates comprising opioid antagonist may be further processed following their formation and prior to admixing with other ingredients to produce a composition of the invention. For example, a dry granulate may be ground or milled using a suitable milling technique to produce particulate material of a smaller size, which may also be sieved to separate the desired size fraction. Wet granulate may be screened to break up agglomerates of granules and remove fine material. In either case, the unused fine material may be reworked to avoid waste. Suitable granulate particle sizes are in the range of about 0.05 mm to about 1.2 mm (e.g. about 1 mm), such as about 0.1 mm to about 1.0 mm (e.g. about 0.8 mm), for example about 0.2 to about 0.6 mm.

Compositions of the invention, once prepared, are preferably directly compressed/compacted into unit dosage forms (e.g. tablets) for administration to mammalian (e.g. human) patients, for example as described hereinafter.

A disintegrating agent, or "disintegrant" may also be included in the composition the invention, particularly those that are in the form of tablets for e.g. sublingual administration. Such an agent may be defined as any material that is capable of accelerating to a measurable degree the disintegration/dispersion of a composition of the invention, and in particular carrier particles, as defined herein. This may be achieved, for example, by the material being capable of swelling and/or expanding when placed in contact with water and/or mucous (e.g. saliva), thus causing tablet formulations/carrier particles to disintegrate when so wetted. Suitable disintegrants include cross-linked polyvinylpyrrolidone, carboxymethyl starch and natural starch and mixtures thereof.

If present, disintegrating agent is preferably employed in an amount of between 0.5 and 10% by weight based upon the total weight of the composition. A preferred range is from 1 to 8%, such as from about 2 to about 7% (e.g. about 5%, such as about 4%) by weight.

It will be evident from the list of possible disintegrants provided above that certain materials may function in compositions of the invention in the form of tablets both as bio/mucoadhesion promoting agents and as disintegrating agents. Thus, these functions may both be provided by different substances or may be provided by the same substance.

When the "same" material is employed as a bio/mucoadhesive and as a disintegrant, ant, the material can be said to be in two separate fractions (a bio/mucoadhesive fraction and a disintegrant fraction). In such instances, it is preferred that the particles within the disintegrant fraction are coarser (i.e. are, relatively speaking, of a larger particle size) than those in the bioadhesive fraction (vide infra).

In any event, the skilled person will appreciate that, in compositions of the invention in the form of tablets, any disintegrant (or disintegrant fraction) will be largely not presented on (i.e. attached to, adhered to and/or associated with) the surfaces of the carrier particles, but rather will be largely presented (i.e. at least about 60%, such as about 70%, e.g. about 80% and, more particularly, about 90% by weight presented) between such particles. Conversely, bio/mucoadhesive (or bio/mucoadhesive fraction) is always largely associated (i.e. is at least about 60%, such as about 70%, e.g. about 80% and, more particularly, about 90% by weight associated) with the carrier particles, that is to say presented on (i.e. attached to, adhered to and/or associated with) the surfaces of the carrier particles, or presented within such particles (vide infra), or both.

Compositions of the invention in the form of tablets for e.g. sublingual administration may also comprise a binder. A binder may be defined as a material that is capable of acting as a bond formation enhancer, facilitating the compression of the powder mass into coherent compacts. Suitable binders include cellulose gum and microcrystalline cellulose. If present, binder is preferably employed in an amount of between 0.5 and 20% by weight based upon the total weight of the tablet formulation. A preferred range is from 1 to 15%, such as from about 2.0 to about 12% (e.g. about 10%) by weight.

Compositions of the invention may comprise a pharmaceutically acceptable surfactant or wetting agent, which may enhance the hydration of active ingredients and carrier particles, resulting in faster initiation of both bio/mucoadhesion and dissolution. If present, the surfactant should be provided in finely dispersed form and mixed intimately with the active ingredients. Examples of suitable surfactants include sodium lauryl sulphate, lecithin, polysorbates, bile acid salts and mixtures thereof. If present, the surfactant may comprise between about 0.1% (e.g. about 0.3%) and about 5% by weight based upon the total weight of the composition, and preferably between about 0.5 and about 3% by weight.

Suitable further additives and/or excipients that may be employed in compositions of the invention, in particular those in the form of tablets for e.g. sublingual administration may comprise:

(a) lubricants (such as sodium stearyl fumarate or, preferably, magnesium stearate). When a lubricant is employed it should be used in very small amounts (e.g. up to about 3%, and preferably up to 2%, by weight based upon the total weight of the tablet formulation);

(b) flavourings (e.g. lemon, menthol or, preferably, peppermint powder), sweeteners (e.g. neohesperidin) and dyestuffs;

(c) antioxidants, which may be naturally occurring or otherwise (e.g. vitamin C, vitamin E, β-carotene, uric acid, uniquion, SOD, glutathione peroxidase or peroxidase catalase); and/or (d) other ingredients, such as carrier agents, preservatives and gliding agents.

Compositions of the invention may be prepared by standard techniques, and using standard equipment, known to the skilled person.

In one embodiment, particles of opioid analgesic may be dry mixed with opioid antagonist-containing carrier particles over a period of time that is sufficiently long to enable appropriate amounts of active ingredients to adhere to the surface of the carrier particles (with or without the presence of bio/mucoadhesion promoting agent).

The skilled person will appreciate that, in order to obtain a dry powder formulation in the form of an interactive mixture, larger carrier particles must be able to exert enough force to break up agglomerates of smaller particles. This ability will primarily be determined by particle density, surface roughness, shape, flowability and, particularly, relative particle sizes.

Standard mixing equipment may be used in this regard. The mixing time period is likely to vary according to the equipment used, and the skilled person will have no difficulty in determining by routine experimentation a suitable mixing time for a given combination of opioid analgesic active ingredient and carrier particle material(s).

Similarly, bio/mucoadhesion promoting agent (if present) may be admixed with opioid antagonist-containing carrier particles may be mixed together with opioid antagonist-containing carrier particles for a sufficient time in order to produce an ordered or interactive mixture. This results in discrete particles of bio/mucoadhesion promoting agent being presented on and/or adhered to the surfaces of the carrier particles.

The bio/mucoadhesion promoting agent suitably has a particle size with a weight based mean diameter of between about 0.1 and about 100 μm (e.g. about 1 and about 50 μm).

Ordered, or interactive, mixtures may also be provided using techniques other than dry mixing, which techniques will be well known to those skilled in the art.

Other ingredients (e.g. disintegrants and surfactants) may be incorporated by standard mixing as described above for the inclusion of active ingredients.

The compositions of the invention may be administered transmucosally, such as buccally, rectally, nasally or preferably sublingually by way of appropriate dosing means known to the skilled person. A sublingual tablet may be placed under tongue, and the active ingredients absorbed through the surrounding mucous membranes.

In this respect, the compositions of the invention may be incorporated into various kinds of pharmaceutical preparations intended for transmucosal (e.g. sublingual) administration using standard techniques (see, for example, Lachman et al, "*The Theory and Practice of Industrial Pharmacy*", Lea & Febiger, 3$^{rd}$ edition (1986) and "*Remington: The Science and Practice of Pharmacy*", Gennaro (ed.), Philadelphia College of Pharmacy & Sciences, 19$^{th}$ edition (1995)).

Pharmaceutical preparations for sublingual administration may be obtained by combining compositions of the invention with conventional pharmaceutical additives and/or excipients used in the art for such preparations, and thereafter preferably directly compressed/compacted into unit dosage forms (e.g. tablets). (See, for example, *Pharmaceutical Dosage Forms: Tablets. Volume* 1, 2$^{nd}$ Edition, Lieberman et al (eds.), Marcel Dekker, New York and Basel (1989) p. 354-356 and the documents cited therein.) Suitable compacting equipment includes standard tabletting machines, such as the Kilian SP300 or the Korsch EKO.

Suitable final sublingual tablet weights are in the range of about 30 to about 400 mg, such as about 40 (e.g. about 50) to about 200 mg, for example about 50 (e.g. about 60) to 180 mg, more preferably between about 60 (e.g. about 70) and about 160 mg. Suitable final tablet diameters are in the range 4 to 10 mm, for example 5 to 9 mm, and more preferably about 6 to about 8 mm.

Irrespective of the foregoing, compositions of the invention should be essentially free (e.g. less than about 20% by weight based on the total weight of the formulation) of water. It will be evident to the skilled person that "premature" hydration will dramatically decrease the mucoadhesion promoting properties of a tablet formulation and may result in premature dissolution of active ingredients.

Wherever the word "about" is employed herein in the context of dimensions (e.g. tablet sizes and weights, particle sizes etc.), surface coverage (e.g. of opioid antagonist-containing carrier particles by particles of opioid analgesic), amounts (e.g. relative amounts of individual constituents in a composition or a component of a composition and absolute doses of active ingredients), it will be appreciated that such variables are approximate and as such may vary by ±10%, for example ±5% and preferably ±2% (e.g. ±1%) from the numbers specified herein.

Compositions of the invention may be administered by way of appropriate dosing means known to the skilled person. For example, a sublingual tablet may be placed under the tongue, and the active ingredients absorbed through the surrounding mucous membrane.

The compositions of the invention are useful in the treatment of pain for example the symptomatic treatment of pain, particularly severe; acute and/or breakthrough pain. According to a further aspect of the invention there is provided a method of treatment of pain which method comprises administration of a composition of the invention to a person suffering from, or susceptible to, such a condition.

For the avoidance of doubt, by "treatment" we include the therapeutic treatment, as well as the symptomatic treatment, the prophylaxis, or the diagnosis, of the condition.

The compositions of the invention enable the production of unit dosage forms that are easy and inexpensive to manufacture, and which enable the rapid release and/or a rapid uptake of the active ingredients employed through the mucosa, such as the oral mucosa, thus enabling rapid relief of pain symptoms, such as those described hereinbefore.

The compositions of the invention also have the advantage that, if injected by an opioid addict, they do not produce the euphoric effects that such an addict seeks and indeed induce opioid withdrawal syndrome.

The compositions of the invention may also have the advantage that they substantially reduce the degree of absorption of active ingredients via swallowed saliva, as well as enabling the administration of "reduced" amounts of the opioid analgesic active ingredient that is employed, so substantially reducing the risk of side effects, as well as intra- and interpatient variability of therapeutic response.

Compositions of the invention may also have the advantage that they may be prepared using established pharmaceutical processing methods and employ materials that are approved for use in foods or pharmaceuticals or of like regulatory status.

Compositions of the invention may also have the advantage that they may be more efficacious than, be less toxic than, be longer acting than, be more potent than, produce fewer side effects than, be more easily absorbed than, and/or have a better pharmacokinetic profile than, and/or have other useful pharmacological, physical, or chemical properties over, pharmaceutical compositions known in the prior art, whether for use in the treatment of pain or otherwise.

The invention is illustrated by way of the following examples.

EXAMPLE 1

Naloxone/Fentanyl—Sublingual Tablets

An ordered mixture of micronised fentanyl citrate and a mucoadhesive component adhered to the surface of water-soluble carrier particles, consisting of a dry granulate of a water-soluble excipient and naloxone hydrochloride is prepared as follows.

Active ingredients are accurately weighed out, along with the other excipients (see below), in appropriate proportions that enable the production of tablets with the absolute amounts of various ingredients mentioned below.

Naloxone hydrochloride (Mallinckrodt, USA) and mannitol (Roquette, France) are mixed in a tumbling mixer (2 L Turbula W. A. Bachofen A G, Basel, Switzerland) for 60 minutes at 32 rpm.

The resultant mixture is then processed in a roller compaction into compacts which are reduced in size by a rotor sieving mill. The particle size of the resultant particles, which are used as carrier particles in the formulation, is larger than 90 µm.

The carrier particles are then mixed with fentanyl citrate (Diosynth, Netherlands) in a tumbling mixer for 72 hours (laboratory scale) at 32 rpm.

Croscarmellose sodium (Ac-Di-Sol®; FMC, USA) and silicified microcrystalline cellulose (ProSolv; Penwest pharmaceuticals Co, USA) are added to the resultant mixture and the mixing is continued for another 30 minutes.

Finally, magnesium stearate (Peter Greven, Netherlands) is added to the mixture and the mixing is continued for another 2 minutes.

The powder mixture is then compacted in a single punch press with 6 mm flat bevel edged punches, to give a tablet weight of 70 mg.

In-process controls, such as tablet weight, crushing strength and disintegration time, are employed, with test samples being withdrawn throughout the tabletting process. Tablets are packaged and labelled.

| One tablet contains - Ingredient | Amount (mg) |
| --- | --- |
| Fentanyl citrate (corresponding to fentanyl base 200 µg) | 0.314 |
| Naloxone hydrochloride (corresponding to naloxone base 8 mg) | 9.77 |
| Mannitol | 49.49 |
| Silicified microcrystalline cellulose | 9.35 |
| croscarmellose sodium | 0.73 |
| magnesium stearate | 0.35 |
| Total tablet weight | 70.00 |

EXAMPLE 2

Naloxone/Fentanyl—Sublingual Tablets
(Incorporating a Dry Granulation Process Step)

Sublingual tablets were made using the same materials, in the same proportions, as those specified in Example 1 above.

Carrier particles were manufactured by mixing mannitol and naloxone HCl in the tumbling mixer at 32 rpm for 60 minutes. Dry granulation was performed by compaction of the mixture in a single punch press (Korsch EKO, Germany) using 20 mm flat-faced punches. The compacts were then crushed by sieving (1.4, 1.0 and 0.8 mm) and a final fraction of 90-800 µm particles was obtained by sieving.

Fentanyl citrate was added to the carrier material in amounts corresponding to a batch size of 300 tablets. Mixing was carried out under the same conditions as those described in Example 1. Croscarmellose sodium and silicified microcrystalline cellulose, and then magnesium stearate, were added and admixed under the same conditions as those described in Example 1.

The mixture was compressed into tablets in the single punch press using 6 mm flat faced bevel edged punches.

EXAMPLE 3

Naloxone/Fentanyl—Sublingual Tablets
(Incorporating a Wet Granulation Process Step)

Sublingual tablets were made using the same materials, in the same proportions, as those specified in Example 1 above.

To make carrier particles, mannitol and naloxone HCl were firstly mixed as described in Example 2 above. 18.5 mL of ethanol was then added to the mixture, the wet mass was sieved (1.0 mm) and the granulate was dried at room temperature for 18 hours. The granulate was then sieved to obtain particles with a fraction of 90-800 µm particles.

Fentanyl citrate, croscarmellose sodium and silicified microcrystalline cellulose, and then magnesium stearate, were all added and admixed under the same conditions as those described in Examples 1 and 2 above. The mixture was compressed as described in Example 2.

What is claimed is:

1. A particulate transmucosal pharmaceutical composition in the form of a tablet suitable for sublingual administration comprising a pharmacologically-effective amount of an opioid analgesic, or a pharmaceutically-acceptable salt thereof, presented in particulate form upon the surfaces of carrier particles comprising a pharmacologically-effective amount of an opioid antagonist, or a pharmaceutically-acceptable salt thereof, which carrier particles are larger in size than the particles of the opioid analgesic, wherein both of said opioid analgesic and said opioid antagonist are delivered transmucosally, wherein the dose of opioid analgesic active ingredient per unit dosage form is in the range of between about 1 μg and about 20 mg, and the dose of opioid antagonist active ingredient per unit dosage form is in the range of between about 0.1 mg and about 4 mg, and wherein the opioid analgesic is selected from the group consisting of fentanyl, alfentanil, sufentanil, remifentanil and buprenorphine, and the opioid antagonist is selected from the group consisting of nalmefene, methylnaltrexone, naltrexone and naloxone.

2. The particulate transmucosal pharmaceutical composition of claim 1, wherein the opioid analgesic is in the form of microparticles.

3. The particulate transmucosal pharmaceutical composition of claim 1, wherein the carrier particles are of a size that is between about 50 and about 1,000 μm.

4. The particulate transmucosal pharmaceutical composition of claim 1, which further comprises a bioadhesion or a mucoadhesion promoting agent, which agent is, at least in part, presented on the surfaces of the carrier particles.

5. The particulate transmucosal pharmaceutical composition of claim 4, wherein the amount of bioadhesion or mucoadhesion promoting agent present is in the range of about 0.1 to about 25% by weight based upon the total weight of the composition.

6. The particulate transmucosal pharmaceutical composition of claim 4, wherein the bioadhesion or mucoadhesion promoting agent has a particle size in the range of about 1 to about 100 μm.

7. The particulate transmucosal pharmaceutical composition of claim 1, wherein the carrier particles further comprise a carbohydrate, a pharmaceutically-acceptable inorganic salt or a polymer.

8. The particulate transmucosal pharmaceutical composition of claim 1, wherein the relative sizes and amounts of the particles of opioid analgesic and the carrier particles that are employed are sufficient to ensure that the carrier particles are at least about 90% covered by the opioid analgesic particles.

9. The particulate transmucosal pharmaceutical composition of claim 1, wherein the composition further comprises a disintegrating agent.

10. The particulate transmucosal pharmaceutical composition of claim 9, wherein the disintegrating agent is selected from the group consisting of crosslinked polyvinylpyrrolidone, carboxymethyl starch, natural starch and mixtures thereof, wherein the amount of disintegrating agent is between about 2 and about 7% by weight based upon the total weight of the composition.

11. A method which comprises administration of the composition of claim 1 to a patient.

12. The method of claim 11, wherein said patient is suffering from or susceptible to pain.

13. The method of claim 12, wherein said pain is selected from the group consisting of severe pain, acute pain and breakthrough pain.

14. The method of claim 11, wherein said composition is resistant to abuse by an opioid addict.

15. The method of claim 11, wherein said patient is an opioid addict.

16. A method of reversing one or more of the pharmacological effects of an opioid analgesic, which method comprises providing for transmucosal administration to a patient the composition of claim 1.

17. The method of claim 16 wherein the pharmacological effect is euphoria.

18. A method of reversing the euphoric effects that may be produced by injection of a composition comprising an opioid analgesic, which method comprises providing for transmucosal administration to a patient the composition of claim 1.

19. A method of treating narcotic drug overdose or diagnosing suspected opioid addiction, which method comprises administering the composition of claim 1 to a patient.

* * * * *

UNITED STATES PATENT AND TRADEMARK OFFICE
CERTIFICATE OF CORRECTION

PATENT NO.         : 8,470,361 B2  
APPLICATION NO.    : 12/312995  
DATED              : June 25, 2013  
INVENTOR(S)        : Pettersson Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this  
Seventh Day of April, 2015

Michelle K. Lee  
*Director of the United States Patent and Trademark Office*